US006562302B1

(12) United States Patent
Hooks, II

(10) Patent No.: US 6,562,302 B1
(45) Date of Patent: May 13, 2003

(54) INCENSE TRAY WITH BLOWER AND PLURALITY OF INCENSE HOLDERS

(76) Inventor: Derry Lee Hooks, II, 10921 Reed Hartman Hwy., Suite 316, Cincinnati, OH (US) 45242

( * ) Notice: Subject to any disclaimer, the term of this patent is extended or adjusted under 35 U.S.C. 154(b) by 328 days.

(21) Appl. No.: 09/624,919

(22) Filed: Jul. 25, 2000

(51) Int. Cl.$^7$ .................................................. A61L 9/03
(52) U.S. Cl. .................... 422/124; 422/126; D11/131.1
(58) Field of Search ............................. 422/124, 126, 422/5, 306; D11/131.1

(56) References Cited

U.S. PATENT DOCUMENTS

| 611,560 | A | | 9/1898 | Chambers ................... 422/125 |
| 931,029 | A | * | 8/1909 | Blood ......................... 422/124 |
| 1,530,103 | A | | 3/1925 | Booth .......................... 422/116 |
| D242,639 | S | | 12/1976 | Patel ............................ D27/15 |
| 4,155,979 | A | | 5/1979 | Powell ........................ 422/126 |
| 4,198,375 | A | | 4/1980 | Rogers ........................ 422/126 |
| 4,219,531 | A | | 8/1980 | Wisniewski ................. 422/124 |
| 4,237,097 | A | | 12/1980 | McDuffie .................... 422/126 |
| 4,324,763 | A | | 4/1982 | Jarman ........................ 422/116 |
| 5,115,821 | A | | 5/1992 | Grooms ....................... 131/238 |
| D341,195 | S | | 11/1993 | Standhardt .................. D23/378 |
| D343,807 | S | | 2/1994 | Newman et al. ........ D11/131.1 |
| D349,954 | S | | 8/1994 | Steiner et al. ............. D23/323 |
| 5,785,061 | A | | 7/1998 | Whiteley ..................... 131/231 |
| 5,873,370 | A | | 2/1999 | Towle et al. ................ 131/190 |
| 5,987,771 | A | | 11/1999 | Curtin ............................ 34/97 |
| 6,050,551 | A | * | 4/2000 | Anderson ............... 422/124 X |
| 6,061,950 | A | * | 5/2000 | Carey et al. ............. 422/126 X |

* cited by examiner

*Primary Examiner*—Elizabeth McKane
(74) *Attorney, Agent, or Firm*—Eric W. Guttag; Hasse Guttag & Nesbitt LLC

(57) ABSTRACT

An incense tray for use with sticks of incense that has a base with an inner surface to receive incense ashes and a housing mounted on the base that has top portion with a screen that permits air to flow from the inside to the outside of the housing. The tray further includes a plurality of incense holders spaced around the periphery of the housing that are angled inwardly towards the center of the tray so that the incense sticks they receive also angle inwardly towards the center. A fan is mounted within the housing to direct the flow of air upwardly through openings in the screen so that the incense smoke is drawn toward the center and then upwardly. A receptacle for receiving a fragrant votive candle or fragrant oil can be mounted on the screen to improve and complement the aromatic effect of the incense smoke.

12 Claims, 3 Drawing Sheets

INCENSE TRAY WITH BLOWER AND PLURALITY OF INCENSE HOLDERS

TECHNICAL FIELD

The present application relates to an incense tray having a blower for directing the incense smoke upwardly. The present application further relates to an incense tray having a plurality of incense holders arranged around the periphery of the tray.

BACKGROUND OF THE INVENTION

A number of devices are described in the art for holding incense sticks that are burned to provide a pleasing aromatic fragrance. One such device is described in U.S. Pat. No. 5,873,370 (Towle et al), issued Feb. 23, 1999, that involves a combination of an incense stick holder, extinguisher and ash tray that is also adapted to store additional incense sticks. A disadvantage of this prior incense device is that the smoke that is generated by the burning incense stick travels in a random fashion, i.e., the smoke cannot be directed as desired by the user. Also, this prior device allows only the use of one stick of incense at a time. Further, removal of the residual ash from trough 36 in the top of lid 32 of this prior device could be potentially difficult and messy because of how narrow it is.

Another incense device is described in U.S. Pat. No. 4,198,375 (Rogers), issued Apr. 15, 1980, that involves an exterior receptacle fitted with an ash collecting basket that supports a lighter for the incense, as well as an axially disposed spindle. This device also includes a disc that is supported by the spindle and has a plurality of circumferentially disposed holes that accept the incense sticks. A wire mesh cap is fitted over this disc so that it can be rotated to permit selective ignition of one or more of the incense sticks. A disadvantage of this prior device is that it is fairly elaborate and complicated. This could again make it difficult and messy to clean up the residual ash. Also, the smoke that is generated by the incense sticks would still travel in a random, undirected fashion.

Another incense device is described in U.S. Pat. No. 5,115,821 (Grooms), issued May 26, 1992, that involves an ashtray having one or more incense holders. Again, the smoke that is generated by the incense sticks in this prior device would still travel in a random, undirected fashion.

Another device for diffusing smoke from various burning materials, including incense, is described in U.S. Pat. No. 4,219,531 (Wisniewski), issued Aug. 26, 1980, and involves a housing having a receptacle for holding the burning material, a fan chamber within the housing into which the smoke can be drawn downwardly from the receptacle through an inlet passage and then forcibly expelled through a side outlet passage by a small battery powered fan located in the fan chamber. A disadvantage of this prior device is that it does not appear to be easily usable with sticks of incense. Also, in drawing smoke downwardly into the chamber and then outwardly through the side outlet passage, residual ash could also be drawn down into the fan chamber, thus making clean up of the device potentially difficult and messy.

Accordingly, it would be desirable to provide an incense device that can be used to burn multiple sticks of incense at the same time, is relatively easy to clean up with regard to residual ash and provides the ability to direct the incense smoke in a specific manner as desired by the user.

SUMMARY OF THE INVENTION

The present invention relates to an incense tray for use with sticks of incense. This incense tray comprises:

(a) a base having an inner surface that is configured to be capable of receiving incense ashes;

(b) a housing associated with the base, the housing having a top portion provided with an air passageway that is capable of permitting the air to flow from the inside to the outside of the housing;

(c) a plurality of incense holders spaced around the periphery of the housing that are capable of receiving a stick of incense, each of the holders being inclined inwardly towards the center of the tray;

(d) a blower mounted within the housing that is oriented to direct the flow of air upwardly through the air passageway provided in the top portion of the housing; and (e) optionally a receptacle mounted on the top portion of the housing that is capable of receiving a fragrant solid or fragrant oil.

The incense tray of the present invention provides a number of advantages over prior incense burning devices. First, this tray allows a plurality of incense sticks to be burned at the same time to provide whatever aroma impact is desired by the user. In addition, these incense holders are inclined inwardly towards the center of the tray so that the incense sticks received by these holders also incline inwardly towards the center of the tray. This, in conjunction with the blower that directs air upwardly through the air passageway in the top portion of the housing, causes the smoke generated by the burning incense sticks to be drawn inwardly and then directed upwardly, thus providing a pleasing aromatic effect. The optional but preferred receptacle for the fragrant solid or fragrant oil provides additional capability for improving and complementing the aromatic effect of the incense smoke.

DETAILED DESCRIPTION OF THE INVENTION

As used herein, the term "incense stick" refers to a piece of wood or other combustible material that is typically coated with a fragrant substance such as a fragrant oil.

As used herein, the terms "fragrant solid" and refer "fragrant oil," refer, respectively, to products that are solid, or fluid or liquid, at room temperature that contain a fragrant substance that is released chemically or by heating of the product. Representative examples of fragrant solids and fragrant oils include votive candles, blocks or cubes of incense, and incense oil.

As used herein, the term "comprising" means various elements, components and steps can be conjointly employed in the present invention. Accordingly, the term "comprising" encompasses the more restrictive terms "consisting essentially of" and "consisting of."

Figure 1:
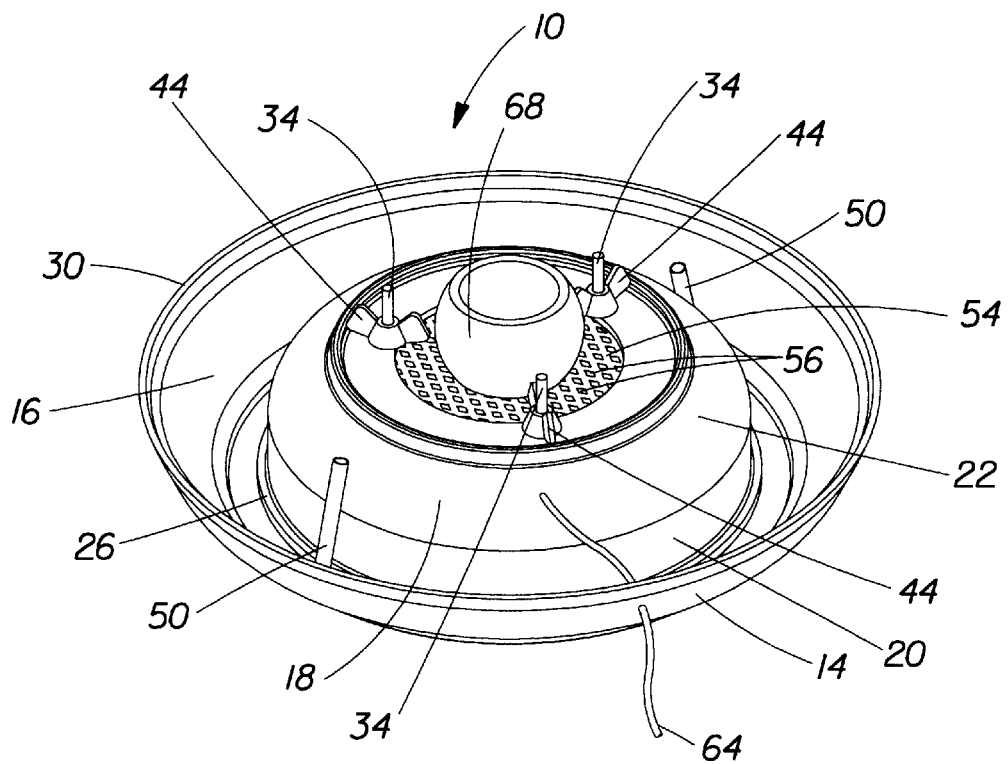
FIG. 1 is a perspective view of an embodiment of the incense tray of the present invention.
Figure 2:
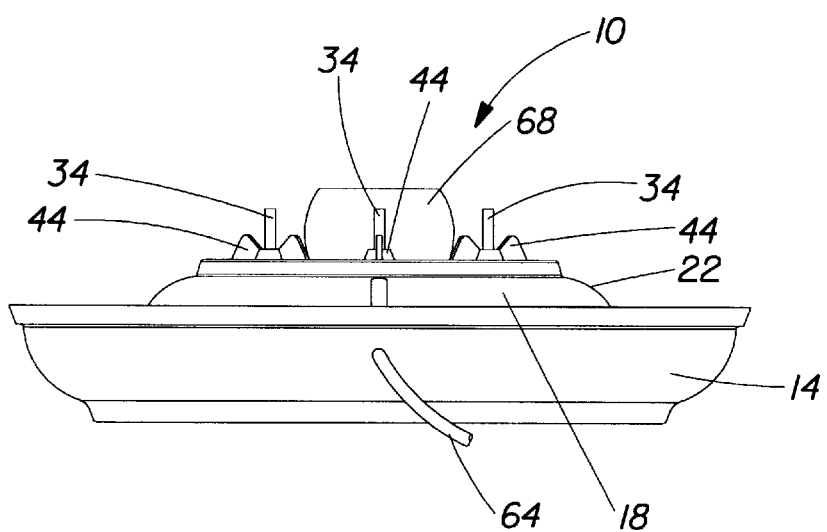
FIG. 2 is a side view of the embodiment of the incense tray of the present invention shown in FIG. 1.
Figure 3:
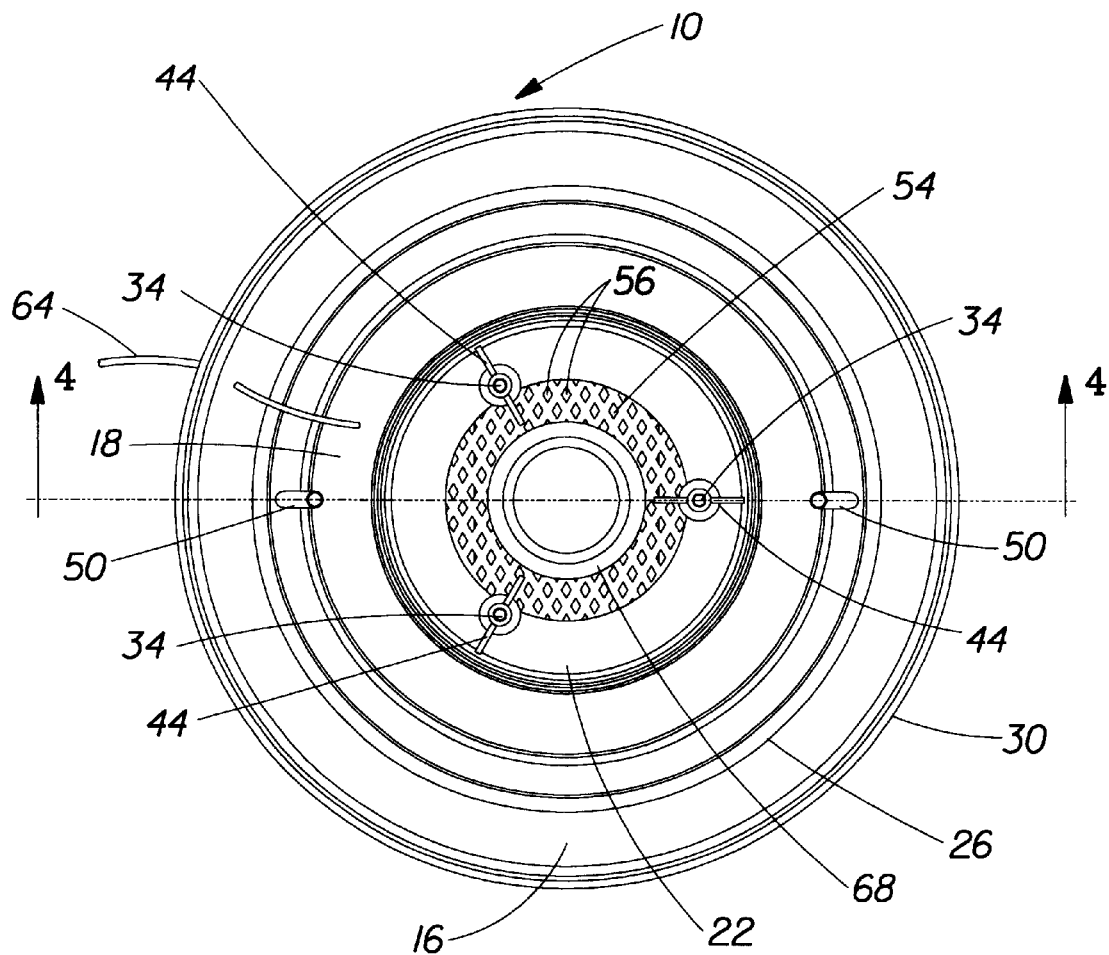
FIG. 3 is top plan view of the embodiment of the incense tray of the present invention shown in FIG. 1.

The present invention and its operation can best be understood by reference to the drawings. FIG. 1 illustrates an exemplary embodiment of the incense tray of the present invention, indicated generally as 10. Tray 10 comprises a circularly shaped base 14 having a concave bowl-shaped inner surface 16 and a circularly shaped housing 18 associated with the base that has a generally cylindrical bottom portion indicated as 20 and a convex bowl-shaped top portion indicated as 22. While base 14 and housing 18 are shown as each having a generally circular configuration, other configurations such as oval or square shapes are also suitable. As also shown in FIGS. 1 and 3, the circular periphery or diameter 26 at the lower end of the bottom portion 20 of housing 18 is sized to be smaller than the circular periphery or diameter 30 of base 14. As a result, the area of inner surface 16 of base 14 between periphery 26 and periphery 30 provides the ability to received the residual incense ash generated during the burning of the incense sticks. Moreover, because of the simplicity of shape of inner surface 16, it is relatively easy to clean or remove the residual incense ash therefrom.

Figure 4:
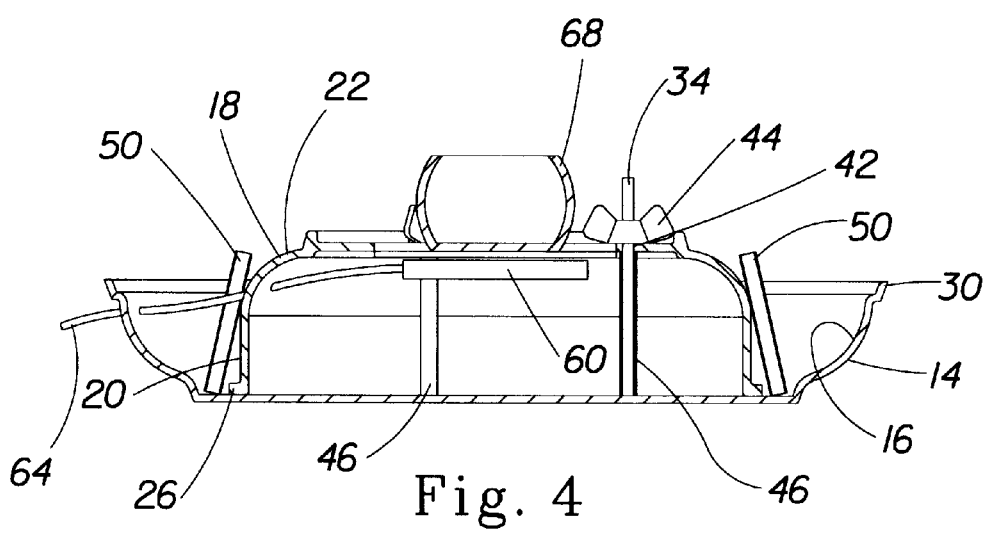
FIG. 4 is a sectional view taken along line 4—4 of FIG. 3.
Figure 5:
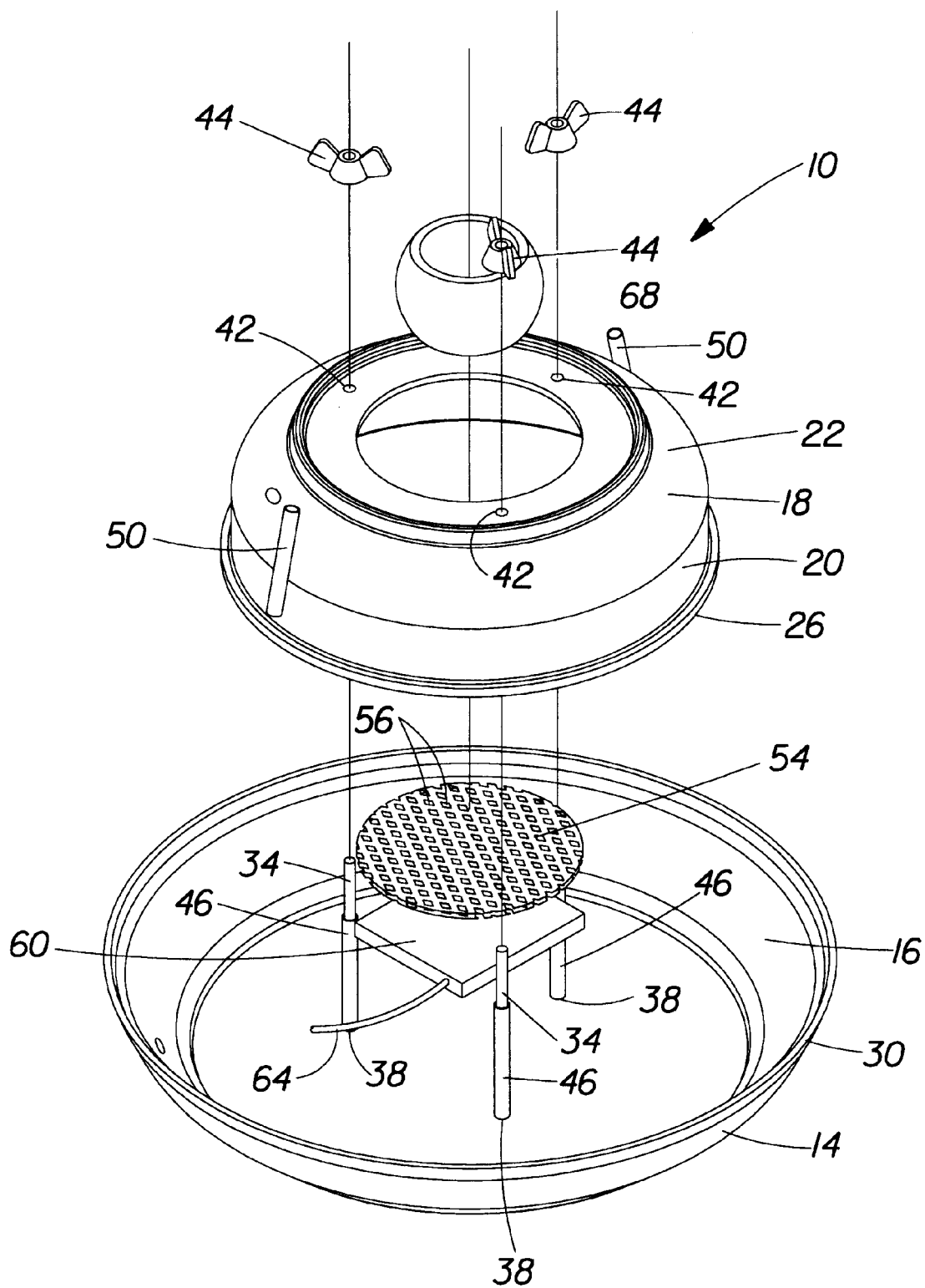
FIG. 5 is an exploded view of the embodiment of the incense tray of the present invention shown in FIG. 1.

As shown particularly in FIGS. 1, 2, 4 and 5, housing 18 is connected to or mounted on base 14 by using fasteners in the form of a combination of a plurality of screws 34 that are inserted, respectively, through a spaced plurality of holes 38 and 42 in base 14 and housing 18. Screws 34 are secured in place by respective wing nuts 44. Although the FIGS. 1, 4 and 5 show the use of three screw 34 and wing nut 44 combinations, different numbers of screw and nut combinations can be used as well. To keep housing 18 at a specific distance above inner surface 16, a plurality of elongated vertical cylindrical spacers 46, each having substantially the same length, are slid onto each of the screws 34.

As shown particularly in FIGS. 1, 3, 4 and 5, a plurality of cylindrical shaped incense holders 50 are spaced around periphery 26 of housing 18. While two holders 50 are shown in the FIGS. 1, 3, 4 and 5 as being mounted at opposites ends of periphery 26, more than two holders 50 can be employed and spaced around the periphery 26 of housing 18 if desired by the user. In addition, while these holders are shown as being connected to or mounted on the periphery 26 of housing 18, these holders could also be connected to or mounted on other elements of tray 10, such as for example, the inner surface 16 of base 14. Also, while holders 50 are shown as having a cylindrical shape, other suitable shapes and configurations such as oval or square shapes can be used as well.

An important aspect of the present invention is to angle holders 50 inwardly so that the incense stick received by the respective holder is also angled inwardly toward the center or vertical axis of the tray 10. The degree to which each of the holders 50 is angled inwardly (relative to the vertical axis of tray 10) can vary but should not be such that the incense stick will easily fall out. Typically, holders 50 are each at an angle of from about 0.5 to about 5°, preferably from about 2 to about 3°, relative the vertical axis of tray 10.

As shown particularly in FIGS. 1, 3 and 5, top portion 22 of housing 18 is provided with an air passageway in the form of a screen indicated as 54 that is secured to the housing in a suitable manner known to the art and has a multiplicity of openings 56. The openings 56 in screen 54 are preferably sized sufficiently large to allow air to flow freely from inside housing 18 to the outside thereof, but sufficiently small to reduce or minimize the amount of incense ash that can fall through and enter the inside of housing 18. Also shown in FIGS. 4 and 5 is a blower in the form of an electrically driven fan 60 that is mounted in a suitable manner inside of housing 18 beneath screen 54 and having wires 64 that can be connected to a suitable battery. Fan 60 is oriented so that is directs the flow of air upwardly through the openings 56 in screen 54. As a result of the upward flow of air, incense smoke generated by the burning incense sticks (positioned in holders 50) is drawn towards the center of tray 10 and is then driven upwardly. This effect is further enhanced by the fact that the incense sticks also lean inwardly towards the center of tray 10 as a result of holders 50 also being angled inwardly.

As shown in FIGS. 1 to 5, tray 10 can also optionally but preferably include a hemispherical bowl-shaped receptacle 68 that is mounted in a suitable manner on top of screen 54. This receptacle 68 can receive fragrant solids or oils such as a fragrant votive candle. This fragrant solid or oil can dispense its fragrance in a time-released fashion either chemically or by internal heating (e.g., by lighting the wick of the votive candle) or can be heated externally to cause the fragrance to be volatilized and dispersed into the air. Alternatively, receptacle 68 can have an upper and lower chamber or section, where the lower chamber contains a heat source such as a candle, while the upper chamber contains a reservoir of fragrant solid or oil that is heated by the candle to volatilize and disperse the fragrance. As a result, this fragrant solid or oil can add to the pleasant aromatic effect provided by the burning incense sticks, especially as a result of the upwardly directed airflow caused by fan 60.

While specific embodiments of the present invention have been described, it will be apparent to those skilled in the art that various modifications thereto can be made without departing from the spirit and scope of the present invention as defined in the appended claims.

What is claimed is:

1. An incense tray, which comprises:
    (a) a base having an inner surface that is configured to be capable of receiving incense ashes;
    (b) a housing associated with the base, the housing having a top portion provided with an air passageway that is capable of permitting air to flow from the inside to the outside of the housing;
    (c) a plurality of incense holders spaced around the periphery of the housing that are capable of receiving a stick of incense, each of the holders being inclined inwardly towards the center of the tray so that the stick of incense received by the respective holder is inclined inwardly towards the center of the tray; and
    (d) a blower mounted within the housing that is oriented to direct the flow of air upwardly through the air passageway.

2. The tray of claim 1 which further comprises a receptacle mounted on the top portion of the housing that is capable of receiving a fragrant solid or fragrant oil.

3. The tray of claim 2 wherein the receptacle has a bowl-shaped configuration.

4. The tray of claim 2 wherein the receptacle comprises a lower chamber and an upper chamber, the lower chamber containing a heat source, the upper chamber containing a reservoir of the fragrant solid or oil.

5. The tray of claim 1 wherein the air passageway is a screen having a multiplicity of openings.

6. The tray of claim 1 wherein the base and the housing each have a circular periphery and wherein the periphery of the housing is sized smaller than the periphery of the base so that the inner surface of the base therebetween is capable of receiving incense ashes.

7. The tray of claim 6 wherein the inner surface of the base is concave bowl-shaped and the top portion of the housing is convex bowl-shaped.

8. The tray of claim 7 which further comprises a plurality of elongated vertical spacers to keep the housing at a specific distance above the inner surface of the base.

9. The tray of claim 1 wherein the incense holders are each at an angle from about from about 0.5 to about 5° relative to the vertical axis of the tray.

10. The tray of claim 9 wherein each of the holders is at an angle of from about 2 to about 3° relative the vertical axis of the tray.

11. The tray of claim 1 which has two incense holders mounted on the periphery of the housing at opposite at ends thereof.

12. The tray of claim 1 wherein each of the incense holders has a cylindrical shape.

* * * * *